(12) United States Patent  (10) Patent No.: US 7,717,847 B2
Smith  (45) Date of Patent: May 18, 2010

(54) SURGICAL HAND ACCESS APPARATUS

(75) Inventor: Robert C. Smith, Cheshire, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 1170 days.

(21) Appl. No.: 11/102,446

(22) Filed: Apr. 5, 2005

(65) Prior Publication Data

US 2005/0267419 A1  Dec. 1, 2005

Related U.S. Application Data

(60) Provisional application No. 60/559,548, filed on Apr. 5, 2004.

(51) Int. Cl.
  *A61B 1/32* (2006.01)
(52) U.S. Cl. ..................................... 600/208
(58) Field of Classification Search ................ 600/184, 600/201–246; 604/104–109, 167.06, 523, 604/533–537, 248, 264, 268, 278, 337–339, 604/164.02, 164.03, 167.01–167.05; 606/213, 606/215–216, 201, 108, 192; 128/850, 855, 128/856, 887, 897
See application file for complete search history.

(56) References Cited

U.S. PATENT DOCUMENTS

| | | | |
|---|---|---|---|
| 2,305,289 | A | 12/1942 | Coburg |
| 3,332,417 | A | 7/1967 | Blanford et al. |
| 3,427,226 | A | 2/1969 | McNeely |
| 3,427,227 | A | 2/1969 | Chamberlin |
| 4,069,913 | A | 1/1978 | Harrigan |
| 4,984,564 | A | 1/1991 | Yuen |
| 5,159,921 | A | 11/1992 | Hoover |
| 5,342,385 | A | 8/1994 | Norelli et al. |
| 5,366,478 | A | 11/1994 | Brinkerhoff et al. |
| 5,368,545 | A | 11/1994 | Schaller et al. |
| 5,480,410 | A | 1/1996 | Cuschieri et al. |
| 5,514,133 | A | 5/1996 | Golub et al. |
| 5,520,610 | A | 5/1996 | Giglio et al. |
| 5,522,791 | A | 6/1996 | Leyva |
| 5,524,644 | A | 6/1996 | Crook |
| 5,526,536 | A | 6/1996 | Cartmill |
| 5,545,179 | A | 8/1996 | Williamson, IV |

(Continued)

FOREIGN PATENT DOCUMENTS

DE  3737121 C2  5/1989

(Continued)

*Primary Examiner*—Cris L Rodriguez
*Assistant Examiner*—Hao D Mai

(57) ABSTRACT

A surgical access apparatus adaptable to permit the sealed insertion of either the surgeon's hand and/or surgical instruments during laparoscopic and endoscopic surgical procedures includes an access housing defining a central longitudinal axis and having a longitudinal opening extending therethrough for passage of a surgeon's hand, a retractor base mounted to the access housing and having a flexible liner for positioning within the incision to engage tissue portions defining the incision, and a trocar adapter which is releasably mounted to the access housing. The trocar adapter includes a trocar sleeve positioned for reception within the longitudinal opening and a trocar valve adapted to receive a surgical instrument in fluid tight relation therewith. The access housing may include a seal adapted to form a seal about each of the surgeon's arm and the trocar sleeve. The seal is adapted to close in absence of the surgeon's arm or the trocar sleeve.

5 Claims, 3 Drawing Sheets

U.S. PATENT DOCUMENTS

| | | | |
|---|---|---|---|
| 5,634,911 | A | 6/1997 | Hermann et al. |
| 5,636,645 | A | 6/1997 | Ou |
| 5,639,937 | A | 6/1997 | Hover et al. |
| 5,640,977 | A | 6/1997 | Leahy et al. |
| 5,649,550 | A | 7/1997 | Crook |
| 5,653,705 | A | 8/1997 | de la Torre et al. |
| 5,672,168 | A | 9/1997 | de la Torre et al. |
| 5,741,298 | A | 4/1998 | MacLeod |
| 5,803,921 | A | 9/1998 | Bonadio |
| 5,810,721 | A | 9/1998 | Mueller et al. |
| 5,813,409 | A | 9/1998 | Leahy et al. |
| 5,832,925 | A | 11/1998 | Rothrum |
| 5,853,395 | A * | 12/1998 | Crook et al. ............ 604/174 |
| 5,899,208 | A | 5/1999 | Bonadio |
| 5,906,577 | A | 5/1999 | Beane et al. |
| 5,947,922 | A | 9/1999 | MacLeod |
| 5,957,913 | A | 9/1999 | de la Torre et al. |
| 5,964,781 | A | 10/1999 | Mollenauer et al. |
| 5,997,515 | A | 12/1999 | de la Torre et al. |
| 6,024,736 | A | 2/2000 | de la Torre et al. |
| 6,033,426 | A * | 3/2000 | Kaji ..................... 606/213 |
| 6,033,428 | A | 3/2000 | Sardella |
| 6,042,573 | A | 3/2000 | Lucey |
| 6,048,309 | A | 4/2000 | Flom et al. |
| 6,077,288 | A | 6/2000 | Shimomura et al. |
| 6,110,154 | A | 8/2000 | Shimomura et al. |
| 6,142,935 | A | 11/2000 | Flom et al. |
| 6,142,936 | A | 11/2000 | Beane et al. |
| 6,149,642 | A | 11/2000 | Gerhart et al. |
| 6,159,200 | A | 12/2000 | Verdura et al. |
| 6,162,172 | A | 12/2000 | Cosgrove et al. |
| 6,238,373 | B1 | 5/2001 | de la Torre et al. |
| 6,254,533 | B1 | 7/2001 | Fadem et al. |
| 6,254,534 | B1 | 7/2001 | Butler et al. |
| 6,315,770 | B1 | 11/2001 | de la Torre et al. |
| 6,319,246 | B1 | 11/2001 | de la Torre et al. |
| 6,382,211 | B1 | 5/2002 | Crook |
| 6,440,063 | B1 | 8/2002 | Beane et al. |
| 6,450,983 | B1 | 9/2002 | Rambo |
| 6,578,577 | B2 | 6/2003 | Bonadio et al. |
| 6,814,700 | B1 | 11/2004 | Mueller et al. |
| 6,840,951 | B2 | 1/2005 | de la Torre et al. |
| 6,846,287 | B2 | 1/2005 | Bonadio et al. |
| 6,908,430 | B2 * | 6/2005 | Caldwell et al. ............ 600/207 |
| 2001/0047188 | A1 | 11/2001 | Bonadio et al. |
| 2002/0019609 | A1 | 2/2002 | McFarlane |
| 2002/0038077 | A1 | 3/2002 | de la Torre et al. |
| 2002/0072762 | A1 | 6/2002 | Bonadio et al. |
| 2004/0015185 | A1 | 1/2004 | Ewers et al. |
| 2004/0049099 | A1 * | 3/2004 | Ewers et al. ............. 600/206 |
| 2004/0092795 | A1 | 5/2004 | Bonadio et al. |
| 2004/0127772 | A1 | 7/2004 | Ewers et al. |
| 2004/0249248 | A1 | 12/2004 | Bonadio et al. |
| 2005/0020884 | A1 | 1/2005 | Hart et al. |
| 2005/0148823 | A1 * | 7/2005 | Vaugh et al. ............. 600/206 |

FOREIGN PATENT DOCUMENTS

| | | |
|---|---|---|
| EP | 0 950 376 A1 | 10/1999 |
| GB | 2 071 502 A | 9/1981 |
| GB | 2 255 019 A | 10/1992 |
| JP | 10-108868 | 4/1998 |
| WO | WO 95/04202 | 2/1995 |
| WO | WO 95/07056 | 3/1995 |
| WO | WO 95/22289 | 8/1995 |
| WO | WO 95/27445 | 10/1995 |
| WO | WO 95/27468 | 10/1995 |
| WO | WO 98/35614 | 8/1998 |
| WO | WO 98/48724 | 11/1998 |
| WO | WO 99/25268 | 5/1999 |
| WO | WO 00/32120 | 6/2000 |
| WO | WO 00/35356 | 6/2000 |
| WO | WO 00/54675 | 9/2000 |
| WO | WO 00/54676 | 9/2000 |
| WO | WO 00/54677 | 9/2000 |
| WO | WO 01/08563 A2 | 2/2001 |
| WO | WO 01/08581 A2 | 2/2001 |

* cited by examiner

SURGICAL HAND ACCESS APPARATUS

CROSS-REFERENCE TO RELATED APPLICATION(S)

This application claims benefit to provisional application No. 60/559,548, filed Apr. 5, 2004, the contents of which are incorporated herein by reference.

BACKGROUND

1. Field of the Disclosure

The present disclosure relates generally to surgical devices for facilitating sealed access across a body wall and into a body cavity and, more particularly, to a surgical access apparatus adaptable to permit the sealed insertion of either the surgeon's hand and/or surgical instruments during laparoscopic and endoscopic surgical procedures.

2. Description of the Related Art

Minimally invasive surgical procedures including both endoscopic and laparoscopic procedures permit surgery to be performed on organs, tissues and vessels far removed from an opening within the tissue. Laparoscopic and endoscopic procedures generally require that any instrumentation inserted into the body be sealed, i.e. provisions must be made to ensure that gases do not enter or exit the body through the incision as, e.g., in surgical procedures in which the surgical region is insufflated. These procedures typically employ surgical instruments which are introduced into the body through a cannula. The cannula has a seal assembly associated therewith. The seal assembly provides a substantially fluid tight seal about the instrument to preserve the integrity of the established pneumoperitoneum.

Minimally invasive procedures have several advantages over traditional open surgery, including less patient trauma, reduced recovery time, reduced potential for infection, etc . . . However, despite its recent success and overall acceptance as a preferred surgical technique, minimally invasive surgery, such as laparoscopy, has several disadvantages. In particular, surgery of this type requires a great deal of surgeon skill in order for the surgeon to manipulate the long narrow endoscopic instruments about a remote site under endoscopic visualization. In addition, in laparoscopic surgery involving the intestinal tract, it is often preferable to manipulate large sections of the intestines to perform the desired procedure. These manipulations are not practical with current laparoscopic tools and procedures accessing the abdominal cavity through a trocar or cannula.

To address these concerns, recent efforts have focused on hand-assisted laparoscopic techniques and procedures. These procedures incorporate both laparoscopic and conventional surgical methodologies. The hand assisted technique is performed in conjunction with a hand access seal which is an enlarged device positionable within the incision in, e.g., the insufflated abdominal cavity. The device includes a seal for forming a seal about the surgeon's arm upon insertion while permitting surgical manipulation of the arm within the cavity. However, known hand access seals are quite cumbersome and incorporate elaborate sealing mechanisms. Moreover, these hand access seals are incapable of conversion for use with laparoscopic instruments.

SUMMARY

Accordingly, the present disclosure relates to a surgical access apparatus adaptable to permit the sealed insertion of either the surgeon's hand and/or surgical instruments during laparoscopic and endoscopic surgical procedures. The access apparatus includes an access housing defining a central longitudinal axis and having a first internal passageway with a first internal dimension configured and dimensioned to permit passage of an object, a seal (e.g., a gel seal) mounted to the housing across the first internal passageway and being adapted to receive the object in substantial fluid-tight relation, and an adapter mountable to the housing. The adapter includes an access member having a second internal passageway defining a second internal dimension less than the first internal dimension of the access housing. Preferably, the first internal passageway of the access housing is dimensioned to permit the passage of a hand of the surgeon while the second internal passageway of the adapter is dimensioned to permit the passage of a surgical instrument. The adapter may include a valve disposed relative to the second internal passageway and being adapted to establish a substantial fluid tight relation with the instrument. The seal of the access housing is adapted to form a substantial fluid tight seal about the access member of the adapter. The adapter may be releasably mounted to the access housing.

In another preferred embodiment, the surgical access apparatus includes an access housing having a first passageway for receiving an object and a base which is mountable to the access housing. The base includes a flexible liner member positionable within an incision of a patient to at least partially line the incision, a first member connected to one end of the liner member and adapted for positioning within the body to engage an inner surface of the body, a second member connected to the other end of the liner member and an expandable member positioned adjacent the access housing to engage the second member of the base. The expandable member is expandable to displace the second member whereby the liner member engages tissue forming the incision to at least partially retract the incision.

The base may include a housing mount mounted to the access housing and positioned adjacent the expandable member. The housing mount may be coupled to the second member of the base and movable relative to the access housing upon expansion of the expandable member to displace the second member. The expandable member may include a balloon member defining an annular shape. The first and second members each also may be resilient annular members.

The access housing may include an outer trough with the expandable member being at least partially accommodated in the outer trough. With this arrangement, the base may include a housing mount coupled to the second member and disposed adjacent the outer trough. The housing mount preferably is adapted to move relative to the access housing, whereby upon expansion of the expandable member, the housing mount is displaced from the first member.

The access housing may have a seal adapted to receive the object in substantial fluid-tight relation. An adapter may be mountable to the access housing. The adapter has an access member defining a second passageway through the seal. The adapter has a valve disposed across the second passageway, and adapted to receive a surgical instrument in substantial fluid-tight relation.

In another preferred embodiment, the surgical access apparatus includes an access housing defining a central longitudinal axis and having a longitudinal opening extending therethrough for passage of a surgeon's hand, a retractor base mounted to the access housing and having a flexible liner for positioning within the incision to engage tissue portions defining the incision, and a trocar adapter which is releasably mounted to the access housing. The trocar adapter includes a trocar sleeve positioned for reception within the longitudinal opening and a trocar valve adapted to receive a surgical instrument in fluid tight relation therewith. The access housing may include a seal adapted to form a seal about the surgeon's arm or the trocar sleeve. The seal is adapted to close in absence of the surgeon's arm or the trocar sleeve. One preferred seal comprises a gel material. The preferred retractor base includes first and second annular members connected to respective ends of the liner. The first annular member is positionable through the incision to engage inner tissue portions within the body cavity. The second annular member is mounted with respect to the access housing. The retractor base may include an expandable member mounted to the access housing and engagable with the second annular member. The expandable member is adapted to expand to displace the second annular member relative to the first annular member to cause the liner to at least partially extract tissue defining the incision.

In one preferred embodiment, the expandable member includes an annular balloon. The retractor base includes an annular mount coupled to the second annular member and positioned relative to the access housing to be engaged by the annular balloon. The annular mount is adapted to more relative to the access housing upon expansion of the annular balloon to displace the second annular member relative to the first annular member.

Methods for performing hand assisted and instrument assisted laparoscopic surgical procedures are also envisioned.

BRIEF DESCRIPTION OF THE DRAWINGS

Preferred embodiments of the present disclosure will be better appreciated by reference to the drawings wherein.

DETAILED DESCRIPTION OF THE PREFERRED EMBODIMENTS

The surgical access apparatus of the present disclosure provides a substantial seal between the body cavity of a patient and the outside atmosphere before, during and after insertion of an object through the apparatus. The apparatus has a flexible liner and an expandable member for retracting the incision so that the apparatus can be used to line the incision and to retract the incision, providing access to a surgical site.

Moreover, the access apparatus of the present invention is capable of accommodating the hand and/or arm of a surgeon and is convertible to receive surgical instruments of varying diameters, which may range from 5 mm to 15 mm, for example, and establishing a gas tight seal with the arm and each instrument when inserted. The access apparatus is further adapted to substantially seal the body cavity in the absence of the object to maintain the integrity of the insufflated peritoneal cavity.

Generally, the access apparatus is convertible between a first operative condition to permit introduction and manipulation of a surgeon's hand or arm in sealed relation therewith and a second operative condition to permit introduction and manipulation of a laparoscopic or endoscopic surgical instrument also in sealed relation.

Although the specific focus of this disclosure will be on a preferred laparoscopic procedure, it will be noted that laparoscopic surgery is merely representative of a type of operation wherein a procedure can be performed in a body cavity through an access apparatus through a body wall.

In the following description, as is traditional the term "proximal" refers to the portion of the instrument closest to the operator, while the term "distal" refers to the portion of the instrument remote from the operator.

Figure 1:
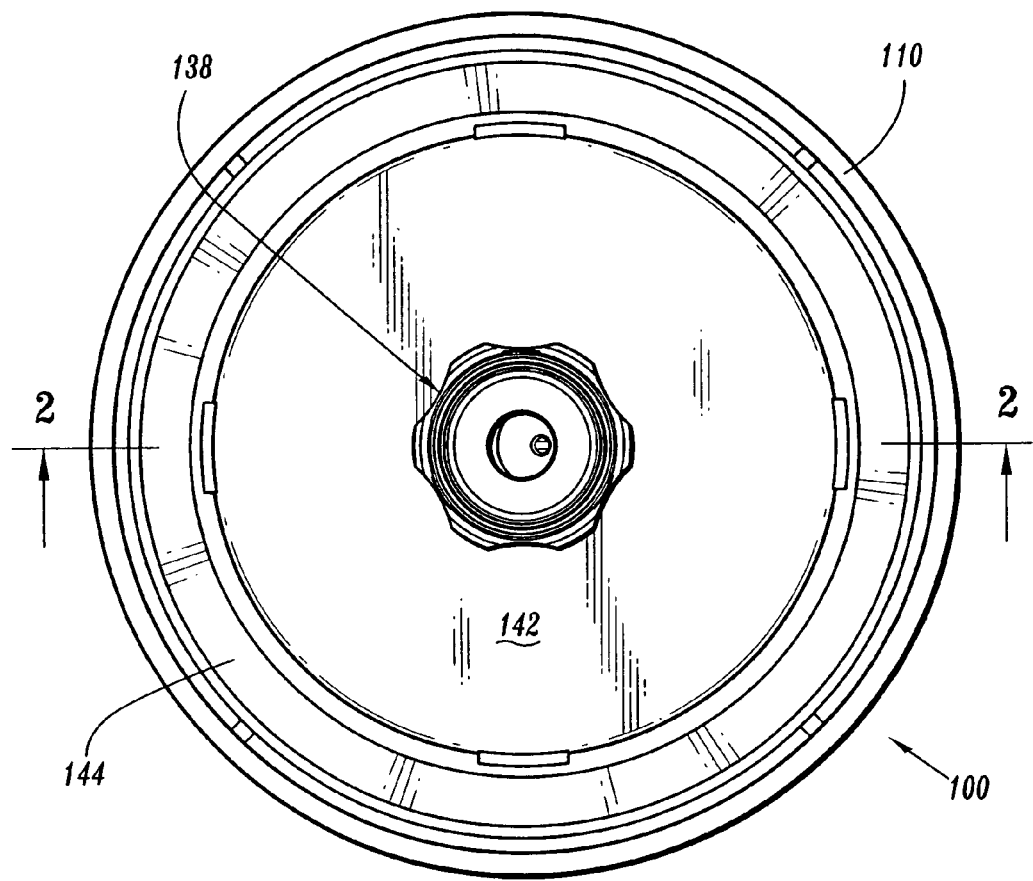
FIG. 1 is a top view of the hand access apparatus in accordance with the principles of the present disclosure illustrating the access housing, trocar adapter and retractor base.
Figure 2:
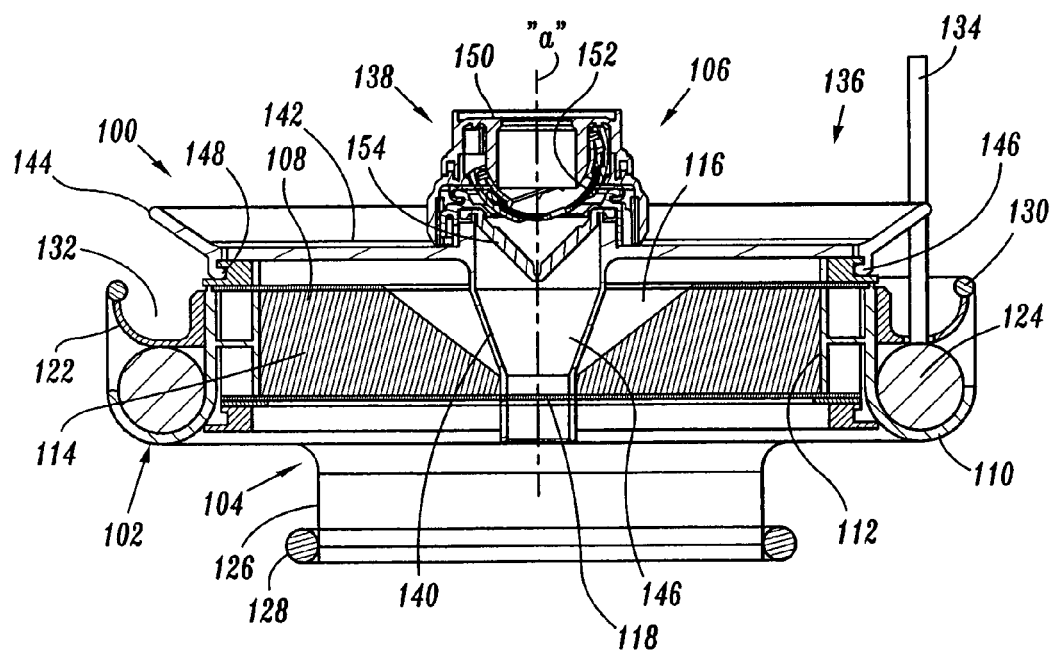
FIG. 2 is a cross sectional view of the access apparatus in accordance with the embodiment of FIG. 1 taken along lines 2-2 of FIG. 1.

Referring now to the drawings, in which like reference numerals identify identical or substantially similar parts throughout the several views, FIGS. 1 and 2 illustrate the access apparatus of the present disclosure. Access apparatus 100 includes two main components, namely, access housing 102 and retractor base 104. The apparatus also desirably includes trocar adapter 106, which is releasably mounted to the access housing 102. Access housing 102 is intended for positioning adjacent (preferably, in contact with) the external area of the body, e.g., the abdominal cavity. Access housing 102 defines central longitudinal axis "a" and longitudinal opening or passageway 108 extending along the central axis "a". Longitudinal passageway 108 defines an internal dimension arranged to permit passage of the surgeon's hand and/or arm. Access housing 102 further includes an outer circumferential U-shaped flange or trough 110 and an internal vertical support wall 112. Vertical support wall 112 defines longitudinal passageway 108. Access housing 102 may be made from any suitable biocompatible material including polycarbonate, polystyrene, ABS, etc. Alternatively, access housing 102 may be fabricated from stainless steel or titanium and their alloys.

Referring still to FIGS. 1-2, access housing 102 preferably includes a seal 114 which is mounted across longitudinal passageway 108. Seal 114 may comprise one or more seals, such as septum seals, flapper valves, duckbill seals, etc., arrangement to provide a substantial seal around a surgeon's arm, or surgical instruments, or in the presence of such object. The embodiment of FIGS. 1-7 has a gel material such as a soft urethane gel, silicon gel, etc. and preferably has compressible characteristics to permit the seal 114 to conform and form a seal 114 about the outer surface of a surgeon's hand and/or arm during insertion and manipulation about the operation site. Seal 114 preferably includes a V-shaped entrance opening 116 which extends to slit 118 within the seal 114. V-shaped opening 116 converges inwardly toward slit 118 to facilitate insertion and passage of an object such as a surgeon's hand and/or adapter 106 through seal 114. Moreover, seal 114 opens to permit passage of the object whereby the internal gel portions defining slit 118 engage this object in fluid tight relation therewith. Seal 114 is further adapted to assume a substantially closed position in the absence of the hand or adapter 106, i.e., to form a zero seal, thus preventing the escape of insufflation gases through access housing 102 when access apparatus 100 in not in use. Slit 118 of seal 114 may be a generally linear orientation, t-shaped, tricuspid, or x-shaped, or other shape. Seal 114 is connected to the interior of access housing 102 through conventional means.

In an alternate preferred embodiment, seal 114 is fabricated from a resilient material, e.g., polyisoprene, and has at least one layer of fabric material positioned adjacent the resilient material, or molded with the resilient material. A friction resisting coating may be applied to seal 114. Seals such as those disclosed in certain embodiments of commonly-assigned U.S. Pat. No. 6,702,787 to Racenet, the contents of which are incorporated in its entirety by reference, may be used. Other valve types are also contemplated including zero-closure valves, septum valves, slit valves, double-slit valves, inflatable bladders, other foam or gel valve arrangements, etc.

Figure 3:
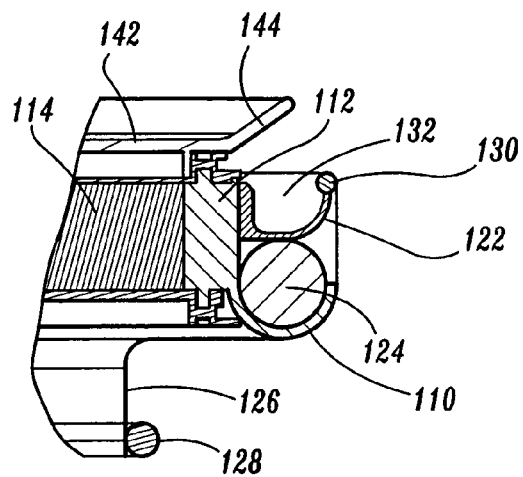
FIG. 3 is a partial cross-sectional view of the access apparatus in accordance with the embodiment of FIG. 1 taken along lines 3-3 of FIG. 1.
Figure 4:
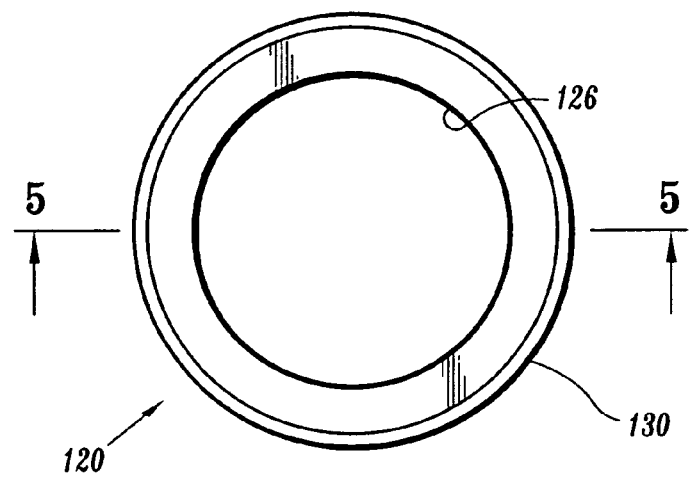
FIG. 4 is a top plan view of the expandable member of the retractor base of the access apparatus in accordance with the embodiment of FIG. 1.
Figure 5:
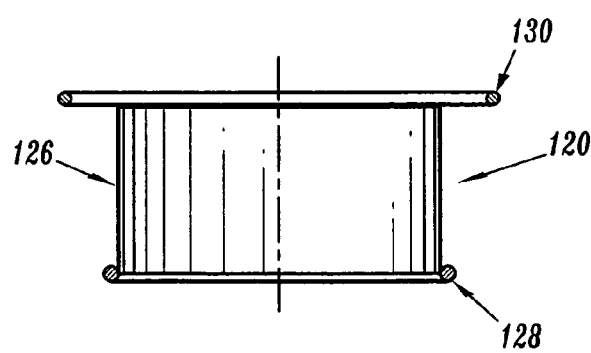
FIG. 5 is a side cross-sectional view of the expandable member in accordance with the embodiment of FIG. 1 taken along lines 5-5 of FIG. 4.

Referring now to FIGS. 1-3, retractor base 104 will be discussed. Retractor base 104 is intended for positioning within the incision of the patient to line the incision and/or retract the tissue defining the incision thereby enhancing access to the underlying body cavity. Retractor base 104 includes liner 120, annular mount 122 and expandable member 124. With reference to FIGS. 4-5, in conjunction with FIGS. 1-3, liner 120 includes tubular sheath or flexible liner member 126, first member 128 connected to one end of the liner member 126 and second member 130 connected to the remaining end of the liner member 126. Liner member 126 may be a sheet of flexible material including, for example, polyethylene, polypropylene, etc., arranged in a tubular configuration. Liner member 126 may also include an elastomeric material and may incorporate rigid runners embedded within the material to increase its rigidity. Although in the preferred embodiment, liner member 126 is tubular, it is envisioned that the liner member 126 may incorporate several pieces, e.g., individual tabs or the like. Liner member 126 may or may not be impervious to fluids. Liner member 126 is adapted to line the incision so as to prevent contamination of the incision by any tissue which may be removed through the access apparatus, or in the course of the surgery. Generally, liner member 126 may also serve to retract the incision during placement of the retractor base 104, so that the patient's skin, fascia, and other tissue are drawn back, allowing access to the surgical site.

First member 128 of liner 120 is adapted for positioning through the incision and beneath the abdominal wall to engage the interior wall portions to thereby secure retractor base 104 relative to the incision. First member 128 is preferably flexible to facilitate passage through the incision and possesses sufficient resiliency to return to its original configuration upon entering the abdominal cavity. First member 128 is preferably annular or ring-like in configuration and may be fabricated from a resilient or elastomeric material. First member 128 may be fixedly secured to the end of liner member 126 through conventional means.

Second member 130 is also annular or ring-like in configuration and is attached to the other end of liner member 126 by conventional means. Second member 130 preferably possesses a more rigid characteristic than first member 128, and may be formed of a suitable polymeric material or a biocompatible metal. Alternatively, second member 130 may be fabricated from an elastomeric material.

As best depicted in FIGS. 2-3, annular mount 122 of retractor base 104 is coaxially mounted about access housing 102. Annular mount 122 is adapted to move relative to access housing 102 in a longitudinal direction relative to longitudinal axis "a" and preferably slides along the outer wall of the access housing 102 adjacent vertical support wall 112. Annular mount 122 is adapted to connect to second member 130 in a manner which secures the second member 130 to the annular mount 122. Any suitable means to connect second member 130 to annular mount 122 are envisioned including adhesives, cements etc. Annular mount 122 and second member 130 may incorporate corresponding structure to securely mount the two components. Such structure may be a tongue and groove arrangement, tab and slot etc. . . . In one preferred embodiment, second member 130 is pulled over to be received within inner channel 132 of annular mount 122 and may be retained within the channel 132 through a friction fit or the like.

Figure 6:
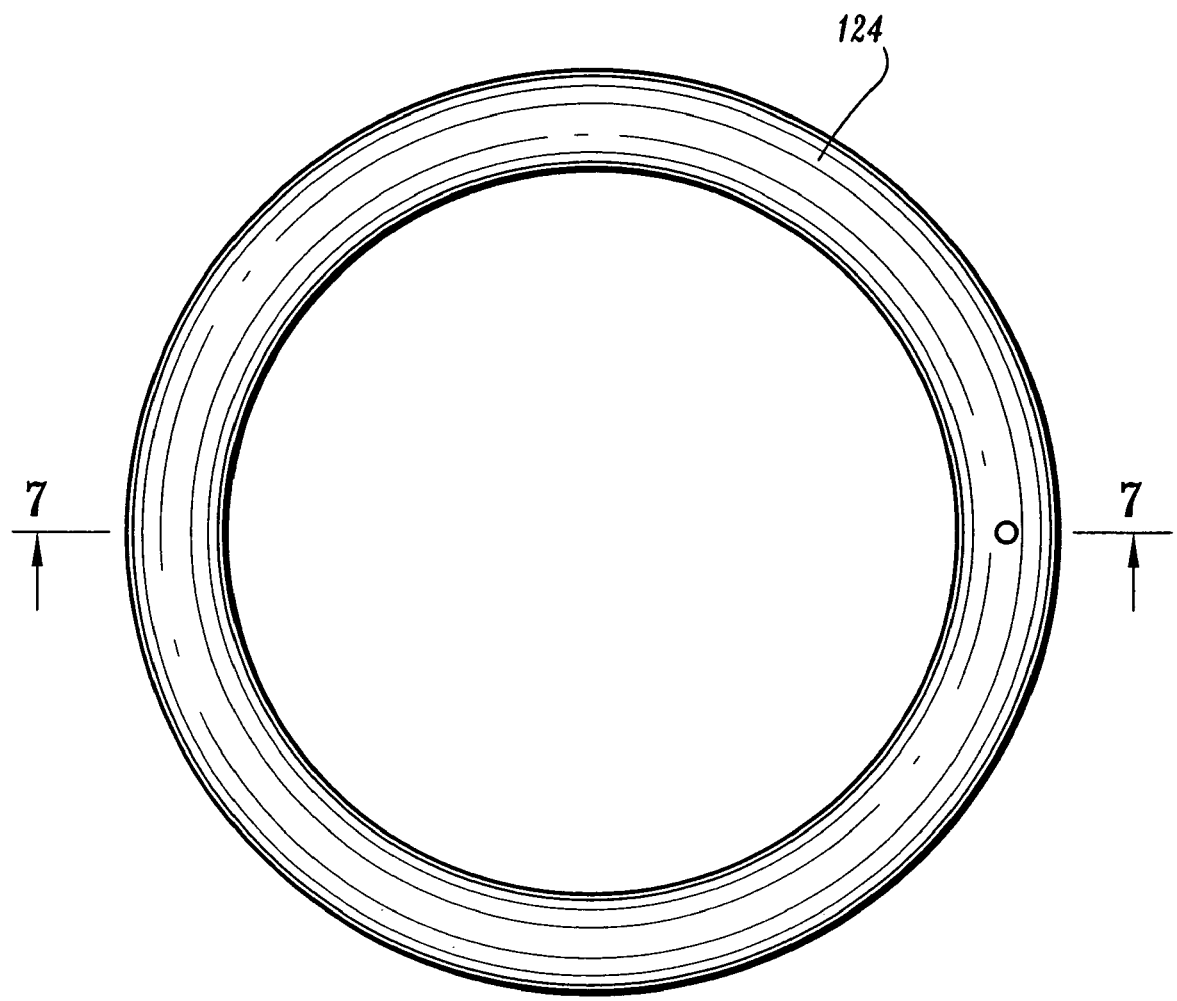
FIG. 6 is a top plan view of the flexible liner of the retractor base of the access apparatus in accordance with the embodiment of FIG. 1.
Figure 7:
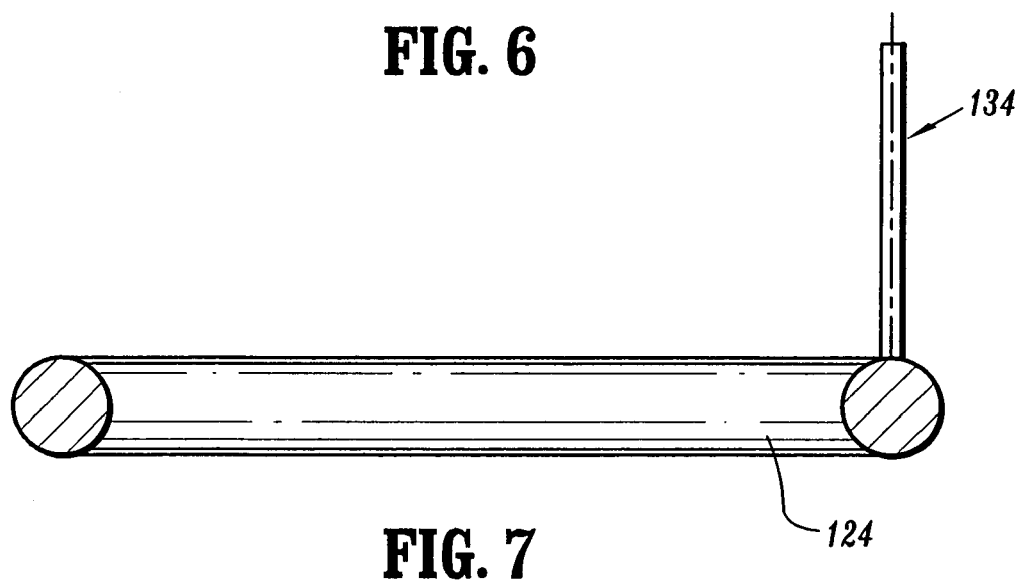
FIG. 7 is a side cross-sectional view of the flexible liner in accordance with the embodiment of FIG. 1 taken along lines 7-7 of FIG. 6.

With reference now to FIGS. 6-7, in conjunction with FIGS. 1-3, expandable member 124 of retractor base 104 is preferably in the form of a surgical balloon having an annular or ring like dimension correspondingly arranged to be received and confined within outer trough 110 of access housing 102. Expandable member 124 includes a fluid supply line 134 which is in communication with the interior of the expandable member 124 to provide fluid to, and selectively inflate, the expandable member 124. Expandable member 124 may be selectively filled with a fluid such as water, saline, etc. or a gas. In the assembled condition of apparatus 100, the upper surface of expandable member 124 contacts annular mount 122. Accordingly, upon expansion of expandable member 124, annular mount 122 is displaced in a proximal direction away from the abdominal cavity. Similarly, second member 130 attached to annular mount 122 also moves proximally away from first member 128. Such movement causes liner member 126 to move toward a tensioned condition to thereby draw the tissue surrounding the incision laterally outwardly to at least partially retract the incision. Liner member 126 is tensioned so as to retract the incision, without requiring the surgeon to pull on the liner member 126, or arrange the liner member 126 and fix the liner member 126 is position. As appreciated, as liner member 126 is tensioned, first member 128 may be also pulled in a proximal direction to bring the first member 128 into contact with the interior wall of the abdominal cavity. This activity effectively secures retractor base 104 within the incision.

Referring again to FIGS. 1-2, trocar adapter 106 of access apparatus 100 will now be described. Trocar adapter 106 includes adapter base 136 and valve assembly 138 which is mounted to the adapter base 136. Adapter base 136 includes trocar sleeve 140, inner wall 142 extending from the sleeve 140 and peripheral flange 144. Trocar sleeve 140 is a tube-like structure having a longitudinal opening 146 defining an internal dimension suitable for passage of surgical instrumentation. The proximal end of trocar sleeve 140 extends beyond inner wall 142 for attachment to valve assembly 138 as will be discussed. Adapter base 136 is preferably monolithically formed as a single unit and may be fabricated from a suitable polymeric material through injection molding techniques. Alternatively, adapter base 136 may be formed of a suitable biocompatible metal material like stainless steel, titanium, titanium alloys etc.

Adapter base 106 is preferably releasably mounted to access housing 102. In one preferred arrangement, adapter base 106 includes peripheral rib 146 extending radially inwardly relative to longitudinal axis "a". Peripheral rib 146 is received within annular groove 148 of access housing 102 in snap-fit relation therewith to releasably connect the two components. Other means for releasably connecting adapter base 106 to access housing 102 are also envisioned including a bayonet coupling, friction fit, tongue and groove, etc. Adapter base 106 may also be tethered to access housing 102 to provide a flip-top arrangement.

Valve assembly 138 may be any conventional trocar seal system adapted for mounting to a trocar sleeve and forming a fluid tight seal about an endoscopic instrument ranging in diameter from about 3 mm to about 15 mm. In one preferred embodiment, valve assembly 138 is of the type available from United States Surgical Corporation of Norwalk, Conn. under the tradename, VERSAPORT™. The VERSAPORT™ seal includes a valve housing 150, a gimbal valve 152 mounted within the housing and a zero-closure or duck-bill valve 154 extending from the valve housing 150 and into trocar sleeve 140. Gimbal valve 152 is adapted to swivel or rotate within valve housing 150 about a central axis of rotation to accommodate offset manipulation of the instrument inserted through valve assembly 138. Duck bill valve 154 is adapted to open in the presence of an instrument and close to function as a zero closure seal in the absence of an instrument. Valve housing 150 is connected to the proximal end of trocar sleeve 140 through any conventional means including adhesives, bayonet coupling, etc. Other valve assemblies for incorporation into adapter 106 are also envisioned such as the valve assemblies disclosed in commonly assigned U.S. Pat. No. 6,482,181, 5,820,600, RE 36,702 and application Ser. No. 09/706,643, filed Nov. 6, 2000, the entire contents of each being incorporated by reference.

Other details of trocar adapter 106 may be ascertained by reference to U.S. patent application Ser. No. 11/101,663, which published as U.S. Patent Publication No. 2005/0222582, which is commonly assigned and was filed concurrently with this application under Express Mail Certificate EU 799732793 US, the entire contents of which application is incorporated herein by reference.

Operation

The use of the access apparatus 100 in connection with a hand assisted laparoscopic surgical procedure will be discussed. The peritoneal cavity is insufflated and an incision is made within the cavity, with e.g., a trocar, to provide access to the cavity as is conventional in the art. Thereafter, retractor base 104 is introduced within the incision by contracting first member 128 and advancing the first member 128 through the incision and into the body cavity. First member 128 is released to permit the first member 128 to return to its normal condition (under the influences of its inherent resiliency) within the cavity. Liner member 126 extends from first member 128 through the incision to line the incision as previously discussed.

The procedure is continued by positioning access housing 102 without adapter 106 adjacent the external body tissue. If not already connected, second member 130 is connected to annular mount 122 by positioning the second member 130 within channel 132 of annular mount 122. Thereafter, expandable member 124 which is received within outer trough 110 of access housing 102 is expanded by introduction of fluids through supply line 134. During expansion, annular mount 122 (through its contact with expandable member 124) is displaced from the patient to slide proximally along the outer wall of access housing 102 to thereby also displace second member 130 of liner 120 in a proximal direction. This movement causes any excess slack in liner member 126 to be removed and may draw first member 128 into engagement with the internal cavity wall thereby securing retractor base 104 relative to the body tissue. As appreciated, liner member 126 may also expand the size of the incision upon movement of second member 130.

With access apparatus 100 in its first operative condition, hand assisted surgery may then be effected by advancement of the surgeon's hand and arm through seal 114 of access housing 102 and into the body cavity. Seal 114 forms a fluid tight seal about the arm. The desired hand assisted procedure may then be performed.

When it becomes desirable to convert hand access apparatus 100 for use with laparoscopic instrumentation (i.e., to convert access apparatus 100 to its second operative condition), trocar adapter 106 is mounted to access housing 102 in the aforedescribed manner. Once mounted, trocar sleeve 140 extends through slit 118 of seal 114. Seal 114 forms a fluid-tight seal about the outer surface of trocar sleeve 140. Instrumentation is introduced through valve assembly 138 and trocar sleeve 140 to carry out the desired procedures. As mentioned, gimbal valve 152 of valve assembly 138 forms a fluid tight seal about the instrument and permits manipulation of the instrument within the operative site.

Thus, access apparatus 100 may be utilized in conjunction with hand-assisted laparoscopic procedures and more conventional instrument-assisted laparoscopic procedures. This flexibility and adaptability significantly reduces the number of incisions required within the abdominal cavity thus minimizing patient trauma and infection, and improving recovery time.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed:

1. A surgical access apparatus which comprises:
    an access housing defining a longitudinal axis and having a first passageway for receiving an object, the access housing including an outer trough; and
    a base mountable to the access housing, the base including:
        a flexible liner member positionable within an incision of a patient to at least partially line the incision;
        a first member connected to one end of the liner member and adapted for positioning within the body to engage an inner surface of the body;
        a second member connected to the other end of the liner member; and
        an expandable member at least partially positioned in the outer trough of the access housing, the expandable member expandable to longitudinally displace the second member of the base relative to the outer trough whereby the liner member engages tissue forming the incision to at least partially retract the incision.

2. The surgical access apparatus according to claim 1 wherein the base includes a housing mount coupled to the second member and disposed adjacent the outer trough, the housing mount adapted to move relative to the access housing, whereby upon expansion of the expandable member, the housing mount is displaced from the first member.

3. The surgical access apparatus according to claim 1 wherein the access housing includes a substantially vertical support wall, the support wall defining the first passageway.

4. The surgical access apparatus according to claim 3 wherein the base includes an annular mount, the annular mount coaxially mounted about the support wall of the access housing, the annular mount operatively connected to the second member, the annular mount adapted for longitudinal movement relative to the support wall and the outer trough upon expansion of the expandable member to displace the second member of the base.

5. The surgical access apparatus according to claim 4 wherein the annular mount is adapted to slide along the support wall of the access housing during the longitudinal movement thereof relative to the support wall and the outer trough.

* * * * *